US012715841B2

(12) United States Patent
Kempter et al.

(10) Patent No.: US 12,715,841 B2
(45) Date of Patent: Aug. 25, 2026

(54) PROCESS FOR THE PRODUCTION OF ALKANESULFONIC ACIDS

(71) Applicant: BASF SE, Ludwigshafen am Rhein (DE)

(72) Inventors: Andreas Kempter, Ludwigshafen (DE); Oliver Sala, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 1177 days.

(21) Appl. No.: 17/632,955

(22) PCT Filed: Jul. 28, 2020

(86) PCT No.: PCT/EP2020/071272
§ 371 (c)(1),
(2) Date: Feb. 4, 2022

(87) PCT Pub. No.: WO2021/023583
PCT Pub. Date: Feb. 11, 2021

(65) Prior Publication Data

US 2022/0332678 A1 Oct. 20, 2022

(30) Foreign Application Priority Data

Aug. 7, 2019 (EP) .................................... 19190499

(51) Int. Cl.
*C07C 303/06* (2006.01)

(52) U.S. Cl.
CPC .................................. *C07C 303/06* (2013.01)

(58) Field of Classification Search
CPC ............................ C07C 303/06; C07C 309/04
See application file for complete search history.

(56) References Cited

U.S. PATENT DOCUMENTS

| | | | | |
|---|---|---|---|---|
| 2006/0100458 | A1 | 5/2006 | Sen et al. | |
| 2019/0276394 | A1* | 9/2019 | Dubois | C07C 303/06 |
| 2022/0194895 | A1* | 6/2022 | Borgmeier | C07C 303/06 |
| 2022/0340518 | A1* | 10/2022 | Piepenbreier | C07C 303/06 |

FOREIGN PATENT DOCUMENTS

| | | | | |
|---|---|---|---|---|
| CN | 1048031 A | 12/1990 | | |
| CN | 1131663 A | 9/1996 | | |
| WO | 2015/071365 A1 | 5/2015 | | |
| WO | WO-2015071455 A1 * | 5/2015 | | C07C 409/44 |
| WO | 2018/096138 A1 | 5/2018 | | |
| WO | WO-2018192954 A1 * | 10/2018 | | C07C 303/06 |
| WO | 2018/208701 A1 | 11/2018 | | |
| WO | 2018/219726 A1 | 12/2018 | | |

OTHER PUBLICATIONS

S. Mukhopadhyay, et al, 147, Studies in surface science and catalysis. 523-528 (2004) (Year: 2004).*
E. A. Robinson, et al, 44 Canadian Journal of Chemistry 1437-1444 (1966) (Year: 1966).*
ThermoFisher (2009)("Fisher") (Year: 2009).*
D.B. Roitman, et al, 39(1) Journal of Chemical and Engineering Data, 39(1), 56-60 (1994) (Year: 1994).*
"Product Safety Summary—Oleum", Solvay, CAS No. 8014-95-7, 2013, 6 pages.
European Search Report for EP Patent Application No. 19190499.4, Issued on Feb. 7, 2020, 3 pages.
International Search Report for PCT Patent Application No. PCT/EP2020/071272, Issued on Sep. 29, 2020, 4 pages.
Robinson, et al., "The Reaction of Methanesulfonic Acid With Sulfur Trioxide", Canadian Journal of Chemistry, vol. 44, Issue 12, Jun. 1966, pp. 1437-1444.

* cited by examiner

*Primary Examiner* — Alexander R Pagano
*Assistant Examiner* — Frank S. Hou
(74) *Attorney, Agent, or Firm* — ArentFox Schiff LLP

(57) ABSTRACT

A process for the manufacturing of alkanesulfonic acid by reaction of an alkane with an anhydride in the presence of sulfuric acid and a starter at ambient temperature or higher and under pressure.

8 Claims, No Drawings

PROCESS FOR THE PRODUCTION OF ALKANESULFONIC ACIDS

CROSS-REFERENCE TO RELATED APPLICATIONS

This application is a National Stage Entry of PCT/EP2020/071272, filed Jul. 28, 2020, which claims priority to EP Application Serial No. 19190499.4, filed Aug. 7, 2019, the disclosures of each of which are hereby incorporated by reference in their entirety.

The present invention relates to a process for the manufacturing of alkanesulfonic acids, in particular methanesulfonic acid (hereinafter "MSA") and to alkanesulfonic acids, in particular MSA, manufactured by said process and its uses.

Alkanesulfonic acids are known to be strong organic acids with similar acid strength compared to inorganic mineral acids like e.g. sulfuric acid. As non-oxidizing and in the case of e.g. methanesulfonic acid, biodegradable acid, these acids, especially methanesulfonic acid are used for a multiplicity of different processes, for example in electroplating industry, in chemical processes or in cleaning applications, or for example in semiconductor industry or as rust and scale remover.

WO 2018/208701 A1 discloses a process for the manufacturing of methanesulfonic acid by reaction of sulfur trioxide with sulfuric acid and methane in the presence of a hydrogen peroxide starter.

In WO 2018/096138 a process for manufacturing of MSA is described, which uses pure $SO_3$ as solvent for the reaction. Additionally, it is claimed, that $SO_3$ can be introduced also in form of oleum with a $SO_3$ content of 50% (w/w) or less, or 65% (w/w) or more.

WO 2015/071455 describes the use of an alkylsulfonylperoxide as starter in the manufacturing of MSA by reaction of methane and $SO_3$, and a process for the manufacture of an alkanesulfonic acid by reaction of an alkane and $SO_3$, especially MSA from methane and $SO_3$. It is claimed, that $SO_3$ is provided via a solution containing $SO_3$/oleum. In particular, methyl-sulfonylperoxide is made in situ from sulfuric acid, MSA and hydrogen peroxide.

In WO2015/071365 a process is described for preparing alkanesulfonic acid from sulfur trioxide and an alkane using a dialkylsulfonyl peroxide, which comprises a step of charging a reactor with sulfur trioxide or a solution thereof.

US 2006/0100458 describes the reaction of methane and $SO_3$ using Marshall's acid, $H_2S_2O_8$, as starter in a mixture of MSA and $SO_3$. The authors achieve selectivities for MSA of over 99% with less than 1% of side products. However, no detailed information is given on the initial reaction mixture.

It is further known e.g. from WO2018/219726 that $SO_3$ reacts with MSA at elevated temperatures in the range of 100° C. to 150° C., however, side products are observed, among others, $CH_3SO_2OSO_2CH_3$ (methane sulfonic acid anhydride, hereinafter "MSAA"), leading to a de-creased yield for MSA. In addition, it is stated, that, as these reactions are equilibrium reactions, distillation leads to undesired MSAA and thus further reduces the yield of MSA.

In the above prior art $SO_3$ was introduced either in pure form as gas or in a liquid form liquid such as in oleum. The addition of pure $SO_3$ or oleum, however, especially at high pressures and temperatures, is potentially dangerous due to the intrinsic properties of $SO_3$.

In Canadian Journal of Chemistry, 1966, 44(12): 1437-1444, Robinson et al. investigated the addition of $SO_3$ to MSA. It was stated, that at low concentrations of $SO_3$, the polysulfonic acid $CH_3S_2O_6H$ is formed initially and which further reacts with MSA to give MSAA. Furthermore, MSAA is stated to be in rapid equilibrium with $H_2S_2O_7$ and higher polysulfuric acids, at higher $SO_3$ concentrations.

In general, handling of $SO_3$ or oleum is difficult and requires multiple safety measures. For example, storage of $SO_3$ or oleum requires temperature control measures. Furthermore, $SO_3$ or oleum tend to outgas; gaseous $SO_3$ reacts with water in the air, which may form undesired depositions in the reactor.

An object of this invention was therefore to find a process for the manufacturing of alkanesulfonic acids, in which the use of pure $SO_3$ or oleum can be avoided, thus making the manufacture of alkanesulfonic acids, in particular of MSA, much easier as well as safety measures less complex.

A further object of this invention was to find a process for the manufacturing of alkanesulfonic acids, where only alkanesulfonic acid or a mixture of alkanesulfonic acids is the sole reaction product.

An additional object of this invention was to find a process for the manufacturing of alkanesulfonic acids starting from the corresponding anhydrides and sulfuric acid, in which additions of $SO_3$ are not hindering the reaction.

The invention, in a further aspect, relates to a process for the manufacturing of alkanesulfonic acid, R—$SO_3$H, ("RSA"), wherein R stands for $C_1$-$C_4$ alkyl, by reaction of an anhydride other than $SO_3$ with sulfuric acid and an alkane, R—H, in the presence of a starter, preferably peroxide starter at ambient temperature or higher and under pressure higher than ambient pressure.

The invention, in another aspect, relates to a process for the manufacturing of alkanesulfonic acid, R—$SO_3$H, ("RSA"), in which the use of pure $SO_3$ or oleum is avoided, wherein R stands for $C_1$-$C_4$ alkyl, by reaction of an anhydride with sulfuric acid and an alkane, R—H, in the presence of a starter, preferably peroxide starter at ambient temperature or higher and under pressure higher than ambient pressure.

The invention also relates to a process for the manufacturing of alkanesulfonic acid, R—$SO_3$H, ("RSA"), wherein R stands for $C_1$-$C_4$ alkyl, by reaction of an anhydride with sulfuric acid and an alkane, R—H, in the presence of a starter, preferably peroxide starter at ambient temperature or higher and under pressure higher than ambient pressure, wherein the anhydride is chosen from the group consisting of $RSO_2OSO_2R$, anhydrides of mineral acids and anhydrides of organic acids, preferably from the group consisting of $RSO_2OSO_2R$, anhydrides of mineral acids other than $SO_3$ and anhydrides of organic acids, more preferably chosen from the group consisting of $RSO_2OSO_2R$ and anhydrides of organic acids.

As mentioned, the anhydride may also be selected from mineral acids, with the exclusion of sulfur trioxide (since it is an aim of the present invention to avoid use of pure $SO_3$ or oleum). Suitable, preferred anyhdrides from mineral acids are listed below.

$C_1$-$C_4$ alkyl stands for methyl, ethyl, n-propyl, i-propyl, n-butyl, sec.-butyl, i-butyl or tert. Butyl, preferably for methyl.

In general, the starter is a peroxide, preferably chosen from the group consisting of aqueous hydrogen peroxide, monomethylperoxydisulfate and salts thereof, dimethylperoxodisulfate and salts thereof, peroxodisulfuric acid and salts thereof, and peroxomonosulfuric acid and salts thereof.

The starter may be added in solid or in liquid form, either in pure form pure or as a solution in a solvent containing sulfuric acid, the RSA or mixtures thereof. Preferably the starter might be added in a liquid form, pure or in a solvent.

As different starters or mixtures of starters can be used, the amount of starter preferably can be expressed in weight-equivalents of pure $H_2O_2$ compared to the total amount of the reaction mixture. Thus, x mol of the used peroxide are regarded as equivalent to x mol of pure $H_2O_2$ (molecular weight: 34 g/mol), which correspond to 34*x g of $H_2O_2$, respectively to (34*x/y)-(wt.-)% (with y being the total mass of the reaction mixture), thus the amount of any used starter can be expressed as $H_2O_2$ equivalent expressed in wt.-% compared to the total amount of the reaction mixture.

The amount of $H_2O_2$ equivalents added to the mixture relative to the total weight of the mixture usually can be chosen in the range from 0.001 to 5.0 wt.-%, preferably in the range from 0.01 to 3.0 wt.-% and most preferably in the range from 0.1 to 2.0 wt.-%.

As a rule, the anhydride is chosen from the group consisting of $RSO_2OSO_2R$, anhydrides of mineral acids and anhydrides of organic acids.

In a very preferred embodiment of this invention as anhydride an alkanesulfonic acid anhydride, $RSO_2OSO_2R$, such as methanesulfonic acid anhydride ("MSAA"), ethanesulfonic acid anhydride, n-propanesulfonic acid anhydride, i-propanesulfonic acid anhydride, n-butanesulfonic acid anhydride, i-butanesulfonic acid anhydride, sec.-butanesulfonic acid anhydride, tert.-butanesulfonic acid anhydride, or mixtures thereof, is chosen, most preferably MSAA, in particular, if the desired product is MSA.

However, also other anhydrides can be used such as e.g. anhydrides of mineral acids (with the exclusion of sulfur trioxide) like $P_2O_5$, $N_2O_5$, or $CO_2$, preferably $P_2O_5$, or anhydrides of organic acids like acetic acid anhydride or maleic acid anhydride. In an especially preferred embodiment of the inventive process, the anyhdride is $P_2O_5$. Additionally, organic anhydrides of the general formula R—(C═O)—O—(C═O)—R' with R' having the same meaning as R, and wherein R and R' can be the same or different, can be used.

A further embodiment of this invention relates to a process for the manufacturing of alkanesulfonic acid, R—$SO_3$H by reaction of an anhydride with sulfuric acid and an alkane, R—H, in the presence of a starter at ambient temperature or higher and under pressure higher than ambient pressure, comprising the following steps:

1) adding a starter to a mixture of the anhydride and sulfuric acid,
2) contacting the alkane to said mixture at a pressure in the range between 10 and 120 bar, preferably between 45 and 120 bar, more preferably between 75 and 110 bar,
3) setting the reaction temperature in the range of 20 to 80° C., preferably 35 to 70° C., most preferably 40 to 65° C., for 1 to 30 hours, preferably from 2 to 20 hours, most preferably from 3 to 15 hours, wherein the starter is chosen from the group consisting of aqueous hydrogen peroxide, monomethylperoxodisulfate and salts thereof, dimethylperoxodisulfate and salts thereof, peroxodisulfuric acid and salts thereof, and peroxomonosulfuric acid and salts thereof, or from mixtures containing one or more of the starter compounds, and wherein the anhydride is chosen from the group consisting of RSO2OSO2R, anhydrides of mineral acids (preferably anhydrides of mineral acids other than $SO_3$), anhydrides of organic acids, and of anhydrides of the general formula R—(C═O)—O—(C═O)—R', where R' has the same meaning as R, and R and R' can be the same or different from each other. Preferably, R stands for methyl, more preferably, R and R' stand for methyl.

A further preferred embodiment concerns the inventive process, wherein the molar ratio of anhydride to sulfuric acid is chosen in the range of from 0.001:1 to 1:1, preferably of from 0.005:1 to 0.80:1, most preferred from 0.01:1 to 0.70:1.

An additional preferred embodiment concerns the inventive process, wherein R—$SO_3$H is added as a further starting material.

Another preferred embodiment concerns the inventive process in which $SO_3$ is added as a further starting material.

In the inventive process, $SO_3$ may additionally be added as an option, which does not seem to influence the reaction negatively.

Thus, it is possible to react a mixture with starter, anhydride and sulfuric acid, a mixture with starter, anhydride, sulfuric acid and R—$SO_3$H, a mixture with starter, anhydride, sulfuric acid and $SO_3$, and a mixture with starter, anhydride, sulfuric acid, $SO_3$ and R—$SO_3$H.

A further preferred embodiment of this invention relates to the inventive process, in which the pressure and/or temperature can be varied during the reaction, e.g. in case the pressure drops because of consumption of the alkane, it might be desirable to adjust the pressure accordingly by adding additional alkane to the reactor. By varying pressure and temperature, a person skilled in the art may wish to avoid negative feedback loops bases on his or her usual knowledge and skill.

An additional aspect of the present invention is also the use of at least one anyhdride, preferably an anhydride other than $SO_3$, in a process for the manufacturing of alkanesulfonic acid, R—$SO_3$H, wherein R stands for $C_1$-$C_4$ alkyl, by reaction with sulfuric acid and an alkane, R—H, in the presence of a starter, preferably peroxide starter, at ambient temperature or higher and under pressure higher than ambient pressure.

In a preferred embodiment of the inventive use, the starter is chosen from the group consisting of aqueous hydrogen peroxide, monomethylperoxydisulfate and salts thereof, dimethylperoxodisulfate and salts thereof, peroxodisulfuric acid and salts thereof, and peroxomonosulfuric acid and salts thereof.

In a further preferred embodiment of the inventive use, the anhydride is chosen from the group consisting of $RSO_2OSO_2R$, anhydrides of mineral acids and anhydrides of organic acids, preferably from the group consisting of $RSO_2OSO_2R$, anhydrides of mineral acids other than $SO_3$ and anhydrides of organic acids, more preferably chosen from the group consisting of $RSO_2OSO_2R$ and anhydrides of organic acids.

In a further preferred embodiment of the inventive use, the anhydride is selected from anyhdrides except $SO_3$.

In general, the inventive process can be carried out in usual vessels such as a reactor or an autoclave. This vessel or reactor or autoclave can be made from any material stable under the reaction conditions, e.g. stainless steel, or steel with a lining like a glass-lining or lining from some polymer like PP, PE, PTFE or others. Preferably a stainless-steel autoclave is used. The vessel can be set-up with or without mixing, internally e.g. with a stirrer or other means, or externally—by means of a pump or any device with comparable functionality (e.g. jet nozzle, injector or the like)—via a mixing device, a heat exchanger, or the like.

After the reaction, the reaction mixture can be worked up by usual means such as cooling down the reaction vessel and decreasing the pressure to ambient pressure.

A preferred embodiment of this invention relates to the inventive process for the manufacturing of MSA, i.e. in which R stands for methyl.

In particular, one embodiment of this invention relates to a process for the manufacturing of MSA by reaction of MSAA with sulfuric acid and methane in the presence of a starter at ambient temperature or higher and under pressure higher than ambient pressure, comprising:

1) adding a starter to a mixture of MSAA and sulfuric acid,
2) contacting the alkane to said mixture at 10 to 120, preferably 45 to 120 bar, more preferably 75 to 110 bar,
3) setting the reaction temperature in the range of 20 to 80° C., preferably 35 to 70° C., most preferably 40 to 65° C., for 1 to 30 hours, preferably from 2 to 20 hours, most preferably from 3 to 15 hours, wherein the starter is chosen from the group consisting of aqueous hydrogen peroxide, monomethylperoxydisulfate and salts thereof, dimethylperoxodisulfate and salts thereof, peroxodisulfuric acid and salts thereof, and peroxomonosulfuric acid and salts thereof, or from mixtures containing one or more of the starter compounds.

Another more preferred embodiment concerns the inventive process for the manufacturing of MSA by reaction of MSAA, wherein sulfuric acid, methane and optionally $SO_3$ and optionally MSA in the presence of a starter at ambient temperature or higher and under pressure higher than ambient pressure, comprising:

1) adding a starter to a mixture of the anhydride, sulfuric acid, optionally $SO_3$ and optionally MSA,
2) contacting the alkane to said mixture at 10 to 120, preferably 45 to 120 bar, more preferably 75 to 110 bar,
3) setting the reaction temperature in the range of 20 to 80° C., preferably 40 to 65° C., for 1 to 30 hours, preferably from 3 to 15 hours, wherein the starter is chosen from the group consisting of aqueous hydrogen peroxide, monomethylperoxydisulfate and salts thereof, dimethylperoxodisulfate and salts thereof, peroxodisulfuric acid and salts thereof, and peroxomonosulfuric acid and salts thereof, or from mixtures containing one or more of the starter compounds.

In the following, the invention is further illustrated in an exemplary way.

EXAMPLES

The samples were characterized by $^{13}$C-NMR spectroscopy using a Bruker Avance III HD 400 MHz ($C_6D_6$ was used in a capillary as the lock reference).

The yield of MSA was calculated by acidimetry: the samples were dissolved in 2-propanol and titrated with a tetrabutylammoniumhydroxide solution. MSA and $H_2SO_4$ were characterized by the obtained titration curves, where at pH turning point #1 the first proton of $H_2SO_4$ and MSA in total, and at pH turning point #2 the second proton of $H_2SO_4$ could be determined.

Example 1: To methanesulfonic acid anhydride (38.48 g, purchased from Apollo) dissolved in sulfuric acid (100%, purchased from Merck) (62.44 g) in an argon filled high pressure stainless-steel reactor (0.3 l volume) equipped with a glass liner, manometer and agitator, 15.254 g of a starter (obtained by adding 10.14 g $H_2O_2$ (70 wt.-%) in small portions to 149.98 g oleum (32 wt.-%) under continuous stirring over one hour and continuous cooling to a temperature in the range of 10 to 18° C.) were added, then nitrogen gas was pressed into the reactor (120 bar) in order to remove oxygen, then pressure was released to normal pressure). Next the reactor was pressurized with methane to 80 bar, the temperature was then raised to 50° C., thereafter the pressure was adjusted to and maintained at 100 bar throughout the reaction by adding additional methane from time to time. After nine hours the reactor was cooled to room temperature, then the pressure was released to normal pressure. A clear, colorless liquid was obtained.

The $^{13}$C-NMR showed only one signal (39.1 ppm), which was assigned to MSA. Based on acidimetry, a yield of more than 97% of MSA was obtained, based on the theoretical amount of $SO_3$ released from the reaction of MSAA with sulfuric acid.

Example 2: To 100 g of a solution consisting of 13 wt.-% methanesulfonic anhydride (purchased from Apollo), 30 wt.-% MSA (Lutropur® MSA 100 from BASF SE), 30 wt.-% $H_2SO_4$ (100% from Merck) and 27 wt.-% $SO_3$ (obtained by distillation from oleum 65 wt.-%, BASF SE), in a argon filled high pressure stainless-steel reactor (0.3 l) equipped with a glass liner, manometer and agitator 0.55 ml of $H_2O_2$ (70 wt.-%) as starter were added. Then nitrogen gas was pressed into the reactor in order to remove oxygen (120 bar), thereafter the pressure was released to normal pressure. Next the reactor was pressurized with methane to 80 bar, the temperature was then raised to 50° C. and finally the pressure was adjusted to and maintained at 100 bar throughout the reaction by adding additional methane from time to time. After eight hours the reactor was cooled to room temperature, then the pressure was released to normal pressure. A clear, colorless liquid was obtained.

The $^{13}$C-NMR data showed only one signal (39.0 ppm), which was assigned to MSA. Based on acidimetry, a yield of more than 93% of MSA was obtained, based on the theoretical amount of $SO_3$ released from the reaction of MSAA with sulfuric acid and $SO_3$ present in the reaction mixture. Thus, the presence of SO3 does not hinder the reaction of the anhydride (other than $SO_3$) to form MSA.

Example 3: Phosphorpentoxide (15.08 g; 99% from Acros), 81.75 g sulfuric acid (100% from Merck) and 15.05 g of the same starter as obtained in example 1 were filled into an argon filled high pressure stainless-steel reactor (0.3 l) equipped with a glass liner, manometer and agitator. Then nitrogen gas was pressed into the reactor in order to remove oxygen (120 bar), thereafter pressure was released to normal pressure. Next the reactor was pressurized with methane to 80 bar, the temperature was then raised to 50° C. and finally the pressure was adjusted to and maintained at 100 bar throughout the reaction by adding additional methane from time to time. After 23.5 h the reactor was cooled to room temperature, then the pressure was released to normal pressure. A clear, colorless liquid was obtained.

The $^{13}$C-NMR data showed only one signal (38.7 ppm), which was assigned to MSA. Based on acidimetry, a yield of more than 90% of MSA was obtained, based on the theoretical amount of $SO_3$ released from the reaction of MSAA with sulfuric acid in the reaction mixture.

The experimental examples show that using certain anhydrides as mentioned in claim 1 of this invention (for example, organic anhydrides like, for example, MSAA) to set free sulfur trioxide from sulfuric acid, works well in a process for manufacturing alkanesulfonic acids from alkane with a peroxide starter. The storage and handling of pure sulfur trioxide and/or oleum may thus be avoided.

Furthermore, it has been shown that using certain other anhydrides, for example from mineral acids, also works in a process for manufacturing alkanesulfonic acids from alkane with a peroxide starter.

The invention claimed is:

1. A process for manufacturing alkanesulfonic acid, R—$SO_3H$, wherein R stands for $C_1$-$C_4$ alkyl, comprising:

combining an anhydride with sulfuric acid and a peroxide starter to form a mixture, wherein the anhydride is $RSO_2OSO_2R$, and combining the mixture with an alkane at ambient temperature or higher and under pressure higher than ambient pressure, wherein the process does not include adding $SO_3$ as a starting material.

2. The process according to claim 1, wherein the starter is aqueous hydrogen peroxide, monomethylperoxydisulfate and salts thereof, dimethylperoxodisulfate and salts thereof, peroxodisulfuric acid and salts thereof, or peroxomonosulfuric acid and salts thereof.

3. The process according to claim 1, comprising:

a) adding the peroxide starter to a mixture of the anhydride and the sulfuric acid, b) contacting the alkane to said mixture at a pressure in the range between 10 and 120 bar, and c) setting a reaction temperature in the range of 20 to 80° C. for 1 to 30 hours.

4. The process according to claim 1, wherein R stands for methyl.

5. The process according to claim 1, wherein a molar ratio of anhydride to sulfuric acid is in the range of from 0.001:1 to 1:1.

6. The process according to claim 1, wherein a molar ratio of anhydride to sulfuric acid is in the range of from 0.005:1 to 0.80:1.

7. The process according to claim 1, wherein a molar ratio of anhydride to sulfuric acid is chosen in the range of from 0.01:1 to 0.70:1.

8. The process according to claim 1, wherein R—$SO_3H$ is added as a further starting material.

* * * * *